(12) United States Patent
Miller et al.

(10) Patent No.: US 10,520,484 B2
(45) Date of Patent: Dec. 31, 2019

(54) AGING TESTING APPARATUS AND USE THEREOF

(71) Applicant: Halliburton Energy Services, Inc., Houston, TX (US)

(72) Inventors: Jeffrey J. Miller, Spring, TX (US); Ketan Chimanlal Bhaidasna, Houston, TX (US); Andrew David Vos, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 247 days.

(21) Appl. No.: 15/386,629

(22) Filed: Dec. 21, 2016

(65) Prior Publication Data

US 2018/0172660 A1    Jun. 21, 2018

(51) Int. Cl.
*G01N 33/28* (2006.01)
*G01N 1/20* (2006.01)
*E21B 41/00* (2006.01)

(52) U.S. Cl.
CPC ......... *G01N 33/2823* (2013.01); *E21B 41/00* (2013.01); *G01N 1/20* (2013.01)

(58) Field of Classification Search
CPC ........................... E21B 41/00; G01N 33/2823
See application file for complete search history.

(56) References Cited

U.S. PATENT DOCUMENTS

| | | | | |
|---|---|---|---|---|
| 1,690,763 A | * | 11/1928 | Wertheimer | A47J 31/06 210/455 |
| 2,217,175 A | * | 10/1940 | Ledbetter | E21B 21/06 73/152.04 |
| 2,449,238 A | * | 9/1948 | Lightfoot, Jr. | B01D 29/085 100/106 |
| 2,646,678 A | * | 7/1953 | Standing | B01D 29/111 210/212 |
| 2,733,595 A | * | 2/1956 | Twining | E21B 21/003 210/289 |
| 4,643,019 A | * | 2/1987 | Jones | G01N 15/0806 73/38 |

(Continued)

OTHER PUBLICATIONS

Omland et al., "Detection Techniques Determining Weighting Material Sag in Drilling Fluid and Relationship to Rheology," Nordic Rheology Society, vol. 15, 2007.

*Primary Examiner* — John Fitzgerald
(74) *Attorney, Agent, or Firm* — Tenley Krueger; C. Tumey Law Group PLLC

(57) ABSTRACT

The embodiments herein relate generally to subterranean formation operations and, more particularly, to enhancing aging testing to characterize settling of particulates in treatment fluids for use in subterranean formation operations. The embodiments use a test cell apparatus comprising a test cell body having an open end for receiving a treatment fluid into an interior of the test cell body, the interior having a floating piston for separating the treatment fluid from a pressurization fluid; a sampling port extending from the open end and having a sample valve for receiving samples of the treatment fluid from the sampling port; a pressure input for pressurizing the interior; and a sealing assembly adapted to be inserted into the test cell body in contact with the interior to fluidly seal the open end and through which the sampling port extends, the sealing assembly comprising a retainable test cell cap.

12 Claims, 3 Drawing Sheets

(56) References Cited

U.S. PATENT DOCUMENTS

| | | | |
|---|---|---|---|
| 5,233,863 A * | 8/1993 | Surjaatmadja | E21B 49/02 73/239 |
| 7,845,212 B1 | 12/2010 | Bi | |
| 7,870,782 B2 * | 1/2011 | Tehrani | G01N 15/06 73/152.07 |
| 8,635,902 B2 | 1/2014 | Jamison et al. | |
| 8,863,567 B2 * | 10/2014 | Jappy | E21B 21/003 73/61.64 |
| 9,206,681 B2 * | 12/2015 | Zhou | G01N 33/2823 |
| 9,341,556 B2 * | 5/2016 | Jamison | G01N 9/00 |
| 9,714,565 B2 * | 7/2017 | Blue | G01N 33/2823 |
| 9,784,667 B2 * | 10/2017 | Lukay | G01N 19/00 |
| 10,180,063 B2 * | 1/2019 | Murphy | G01N 33/2823 |
| 10,209,169 B2 * | 2/2019 | Jamison | G01N 9/00 |
| 2004/0124153 A1 * | 7/2004 | van de Weijer | B01D 15/02 210/688 |
| 2004/0164005 A1 * | 8/2004 | Allen, III | B03B 5/34 209/725 |
| 2008/0236253 A1 * | 10/2008 | Tehrani | G01N 15/06 73/38 |
| 2010/0133204 A1 * | 6/2010 | Tehrani | G01N 33/2823 210/785 |
| 2011/0120217 A1 * | 5/2011 | Huynh | G01N 15/08 73/152.22 |
| 2011/0130965 A1 * | 6/2011 | Slater | E21B 21/01 702/9 |
| 2013/0312511 A1 * | 11/2013 | Jamison | G01N 9/00 73/152.05 |
| 2014/0216149 A1 * | 8/2014 | Zhou | E21B 47/00 73/152.18 |
| 2015/0135815 A1 * | 5/2015 | Blue | G01N 15/0806 73/152.18 |

* cited by examiner

AGING TESTING APPARATUS AND USE THEREOF

BACKGROUND

The embodiments herein relate generally to subterranean formation operations and, more particularly, to enhancing aging testing to characterize settling of particulates ("sag") in treatment fluids for use in subterranean formation operations.

During the performance of various subterranean formation operations (e.g., drilling, completion, and the like), numerous treatment fluids are generally employed. As used herein, the term "treatment fluid" refers to any fluid that may be used in a subterranean application in conjunction with a desired function and/or for a desired purpose. The term "treatment fluid" does not imply any particular action by the fluid or any component thereof.

During the drilling of a wellbore in a subterranean formation, a drilling treatment fluid (or simply "drilling fluid") is circulated as a drill bit bores through the formation to form the wellbore. The drilling fluid is specially designed to remove drill cuttings from the wellbore, cool and lubricate the drill bit, aid in support of the drill pipe and drill bit, provide hydrostatic head to maintain the integrity of the wellbore walls and prevent well blowouts, and the like. Drilling fluids are designed based on the specific characteristics of a particular subterranean formation, and may be water-based, oil-based, or an emulsified fluid.

The density of the drilling fluid is closely maintained in order to control the hydrostatic pressure that the fluid exerts at the bottom of the well. If the drilling fluid is too light (e.g., lacking sufficient density), formation fluids, which are at higher pressures than the hydrostatic pressure developed by the drilling fluid, can enter the wellbore and flow uncontrolled to the surface, possibly causing a blowout. If the mud is too heavy (e.g., exhibiting excessive density), then the hydrostatic pressure exerted at the bottom of the wellbore can reduce the rate at which the drill bit will drill the hole, increasing the time and cost of the drilling operation. Further, excessive fluid density (or "weight") can fracture the formation causing wellbore failures and depletion of the drilling fluid to the formation, resulting again in time and cost associated with the drilling operation.

To achieve the desired density of a drilling fluid, particulate weighting agents may be added thereto. Such particulates are prone to settling (also referred to as "sag") in drilling fluids during drilling and completion operations, which can result in an alteration of the density of the drilling fluid, resulting in the various problems previously described, among others. Such settling accordingly may result in large density variations throughout a wellbore column, typically where larger densities are toward the bottom of the wellbore and lighter densities on the top.

Manual aging tests (static and dynamic) are generally used to determine the sag property of a particular drilling fluid in which a syringe is used to manually withdraw samples from a portion of a container (e.g., a top portion), which limits the density measurement to the particular area and may introduce experimental error (e.g., agitation of the weighting agents in the fluid by manual introduction of the syringe). These tests may also be time-consuming relative to other fluid measurements. Often, structural limitations of existing aging tests also prevent experimental observation at high temperatures and pressures.

Manual aging tests may also lack a suitable method to assess the flow behavior of a treatment fluid. Treatment fluids may have suitable suspension of weight materials, for instance, but excessive gelation which may cause, for example, difficulty when the treatment fluid is to be removed or displaced from annular spaces. This fluid flow behavior information, at high temperatures and pressures during the aging process or after aging at these conditions, provides a key indication of success in certain downhole operations, such as well logging operations, cementing, flow back completions, and the like.

BRIEF DESCRIPTION OF THE DRAWINGS

The following figures are included to illustrate certain aspects of the embodiments described herein, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
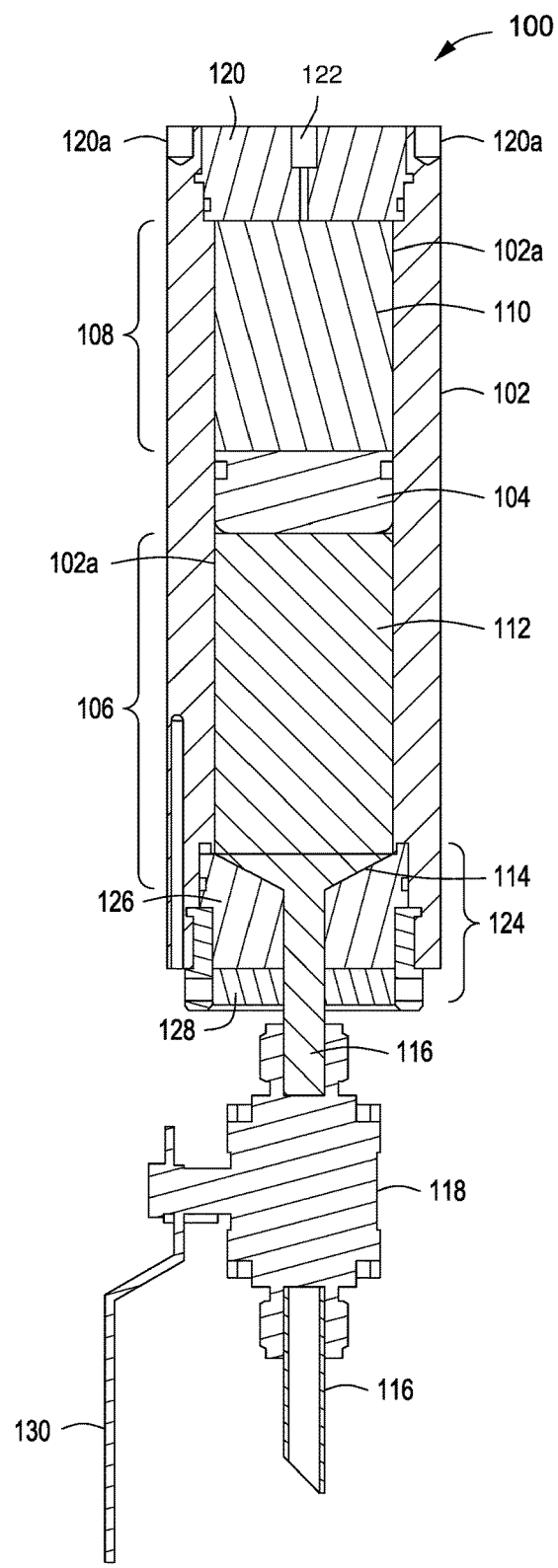
FIG. 1, illustrates a planar view of a test cell apparatus 100, according to one or more embodiments of the present disclosure.

The embodiments herein relate generally to subterranean formation operations and, more particularly, to enhancing aging testing to characterize settling of particulates ("sag") in treatment fluids for use in subterranean formation operations.

The embodiments of the present disclosure provide for enhanced aging testing for treatment fluids subject to particulate sag that influences the density and viscosity of the treatment fluid. The embodiments provide a test cell apparatus and methods of use thereof to improve accurate and effective density and viscosity measurements on treatment fluids. The present embodiments further enable representative aging testing at temperatures and pressure representative of actual subterranean formation conditions. Accordingly, the test cell apparatus and methods of use provided herein are able to assess the suspension capabilities of various treatment fluids over time and over a fluid column, thereby contributing pivotally to the design of these highly technical treatment fluids to ensure optimization of their suspension capacity based on the test results.

Advantages of the test cell apparatus and methods of the present disclosure are provided herein. It employs an inverted cell body that is equipped with a fluid sampling port at the bottom of the test cell. Aging is conducted by allowing elevating temperature, elevating pressure, or a combination thereof for a period of time and thereafter the bottom of the fluid column is accessible to testing. The density and viscosity of the bottom fluid portion can then be evaluated compared to the original sample. Accordingly, a variety of times, temperatures, and pressures can be used to determine the suspension characteristics of the particular treatment fluid being tested. The ability to test the "tell-tale," revealing, bottom stratum of fluids during aging testing by the test apparatus and methods described herein allows accurate sagging measurements to be used to design treatment fluids, which has heretofore not been performed without manual intervention that may disturb the accuracy of the sample or result in such a small amount of volume that inaccurate and unrepresentative measurements are obtained.

One or more illustrative embodiments disclosed herein are presented below. Not all features of an actual implementation are described or shown in this application for the sake of clarity. It is understood that in the development of an actual embodiment incorporating the embodiments disclosed herein, numerous implementation-specific decisions must be made to achieve the developer's goals, such as compliance with system-related, lithology-related, business-related, government-related, and other constraints, which vary by implementation and from time to time. While a developer's efforts might be complex and time-consuming, such efforts would be, nevertheless, a routine undertaking for those of ordinary skill in the art having benefit of this disclosure.

It should be noted that when "about" is provided herein at the beginning of a numerical list, the term modifies each number of the numerical list. In some numerical listings of ranges, some lower limits listed may be greater than some upper limits listed. One skilled in the art will recognize that the selected subset will require the selection of an upper limit in excess of the selected lower limit. Unless otherwise indicated, all numbers expressing quantities of ingredients, properties such as molecular weight, reaction conditions, and so forth used in the present specification and associated claims are to be understood as being modified in all instances by the term "about." As used herein, the term "about" encompasses +/−5% of a numerical value. For example, if the numerical value is "about 5," the range of 4.75 to 5.25 is encompassed. Accordingly, unless indicated to the contrary, the numerical parameters set forth in the following specification and attached claims are approximations that may vary depending upon the desired properties sought to be obtained by the exemplary embodiments described herein. At the very least, and not as an attempt to limit the application of the doctrine of equivalents to the scope of the claim, each numerical parameter should at least be construed in light of the number of reported significant digits and by applying ordinary rounding techniques.

While compositions and methods are described herein in terms of "comprising" various components or steps, the compositions and methods can also "consist essentially of" or "consist of" the various components and steps. When "comprising" is used in a claim, it is open-ended.

As used herein, the term "substantially" means largely, but not necessarily wholly.

The use of directional terms such as above, below, upper, lower, upward, downward, left, right, uphole, downhole and the like are used in relation to the illustrative embodiments as they are depicted in the figures herein, the upward direction being toward the top of the corresponding figure and the downward direction being toward the bottom of the corresponding figure, the uphole direction being toward the surface of the well and the downhole direction being toward the toe of the well. Additionally, the embodiments depicted in the figures herein are not necessarily to scale and certain features are shown in schematic form only or are exaggerated or minimized in scale in the interest of clarity.

The embodiments described herein employ a test cell apparatus and aging testing method using the test cell apparatus to determine density and viscosity measurements of treatment fluids. Although the test cell apparatus and methods described below use drilling treatment fluids as an example for illustration purposes, it is to be appreciated that any treatment fluids for use in a subterranean formation operation that employ particulates to impart density or viscosity may be tested using the test cell apparatus and methods described herein. Such treatment fluids may be drilling treatment fluids, completion treatment fluids, stimulation treatment fluids (e.g., fracturing, frac-packing, gravel packing), production treatment fluids, enhanced oil recovery treatment fluids, and the like, without departing from the scope of the present disclosure.

Common additives included in one or more of the above referenced treatment fluids to affect density and viscosity may include, but are not limited to, weighting agents (densifier), salts (densifier), viscosifying agents (viscosifier), filtration control agents (viscosifier to control filtration rate), wetting agents (to preferentially modify solids surfaces), suspending agents, emulsifiers, and the like, and any combination thereof.

Examples of such weighting agents may include, but are not limited to, barite, galena, iron oxide, calcite, hematite, siderite, celesite, dolomite, magnetite, manganese tetroxide, illmenite, and the like, and any combination thereof. Examples of salts included in treatment fluids to affect density may include, but are not limited to, sodium chloride, sodium bromide, potassium chloride, potassium bromide, calcium chloride, zinc bromide, and the like, and any combination thereof. Viscosifiers are typically clays and natural or synthetic polymers, which may include, but are not limited to, bentonite, sepiolite, attapulgite, organic clays, sodium alluminosilicates, calcium alluminosilicates, hydrous magnesium silicate, hydrous magnesium aluminum silicate, and the like, and any combination thereof. Filtration control agents may overlap with the viscosifiers because the more viscous a fluid is that is being forced through a filter cake, the lower the filtration rate. Examples of filtration control agents may include, but are not limited to, polymers, starches, and the like, and any combination thereof.

Examples of wetting agents for use in the treatment fluids described herein may include, but are not limited to, various surfactant compounds with long hydrocarbon chain fatty acids, derivatives of fatty acids, fatty acid polyamides, sulfonate salts, triglycerides, phospholipids, and the like, and any combination thereof. Suspension agents may include, but are not limited to, amine-modified clays, various clay minerals, organic polyacids and derivatives, polymers, and the like, and any combination thereof. Examples of emulsifiers or emulsifying agents may include, but are not limited to, fatty acids, blends including modified fatty acids and rosin acids, polyamines and polyamides, ethoxylated compounds, among other surfactants with hydrophilic and lipophilic groups, and the like, and any combination thereof.

Drilling and other applicable treatment fluids must be designed to maintain appropriate equivalent circulation density and good particulate suspension (e.g., weighting agents), and thus testing of such measurements is imperative. These two aims may contradict each other, as lower circulating pressure loss from a reduced viscosity may also lead to reduced suspension capacity. Also, it is desirable to have suitable fluid flow behavior (e.g., easy to initiate movement, minimum shear strength, and the like) in the treatment fluid so that subsequent operations can be conducted successfully without causing the buildup of high downhole pressures. As used herein, the term "fluid flow behavior" or simply "flow behavior," and grammatical variants thereof, refers to the flow response of a fluid to an applied force or pressure. It is of particular importance to understand how treatment fluids may behave at advanced temperatures and pressures after aging for extended time periods that represent well operational conditions. These may include, for example, prolonged static exposure in a wellbore or annulus due to inclement weather, rig maintenance, and associated activities involved with completing the well. The embodiments herein permit efficient and accurate testing to ensure that the design of such treatment fluids is based on true data, rather than assumptions.

Referring now to FIG. 1, illustrated is a planar view of a test cell apparatus 100, according to one or more embodiments of the present disclosure. As shown in FIG. 1, the test cell apparatus 100 includes a test cell body 102, which is shown in section to demonstrate generally the interior 102*a* of the test cell apparatus 100 in operation (i.e., in the state in which a sample treatment fluid would be tested). The test cell body 102 may be a generally cylindrical, tubular structure having an interior 102*a* including a floating piston 104 and capable of holding various fluids, as described below. It will be appreciated, however, that other geometrical configurations of the interior 102*a* of the test cell body 102 are possible, such as conical or otherwise curving, without departing from the scope of the present disclosure.

In some embodiments, the interior 102*a* of the test cell body 102 has a total volume of from about 0.1 liters (L) to about 2.0 L, encompassing any value and subset therebetween. In some embodiments, the diameter of the interior 102*a* (i.e., the inner diameter) of the test cell body 102 is generally consistent throughout the majority (>50%) of the interior 102*a* of the test cell body 102 to mimic subterranean formation wellbores, with some exception embodiments, as described below (e.g., tapered open end).

In operation, the interior 102*a* of the test cell body 102 comprises a lower section 106 and an upper section 108 having the floating piston 104 disposed therebetween. The floating piston 104 floats within the test cell body 102 and separates and isolates a pressurization fluid 110 from an introduced treatment fluid 112 to be tested (e.g., a drilling fluid comprising weighting agents). It will be appreciated that the floating piston 104 and the pressurized fluid 110 may be displaced at any location in the lower section 106 of the interior 102*a* of the test cell body 102 when no treatment fluid 112 is included therein. Generally, the volume of pressurization fluid 110 is included in the interior 102*a* of the test cell body 102 such that the floating piston 104 is located at or above the midsection of the interior 102*a* of the test cell body 102 upon introduction of the treatment fluid 112 into the test cell body 102. In some embodiments, the volume of pressurization fluid 110 is of from about 1% to about 99% of the volume of the interior 102*a* of the test cell body 102, encompassing any value and subset therebetween. The remaining volume of the interior 102*a* of the test cell body 102 is then filled with the treatment fluid 112, which displaces the floating piston 104 and the pressurization fluid 110 to the upper section 108 of the interior 102*a* of the test cell body 102. Accordingly, the amount of treatment fluid 112 tested can vary to encompass various volumes and further expand the functionality of the embodiments described herein.

The interior 102*a* of the test cell body 102 comprises an open end 114 at the bottommost portion of the lower section 106 thereof. In some embodiments, as shown, the open end 114 may be tapered to permit ease of sampling of a treatment fluid after aging testing, without departing from the scope of the present disclosure. It will be appreciated, however, that other configurations, including where the open end 114 maintains the inner diameter of the entire interior 102*a* of the test cell body 102 may also be appropriate, without departing from the scope of the present disclosure. In preferred embodiments, the open end 114 is tapered.

The open end 114 (whether tapered or otherwise) is fluidly coupled to a sampling port 116 extending therefrom. As used herein, the term "fluidly coupled," and grammatical variants thereof, refers to fluid (i.e., liquid or gas) flow between at least two elements without significant or any seepage to the external environment. In some embodiments, the open end 114 of the test cell body 102 and the sampling port may be composed of a continuous material. In other embodiments, the open end 114 of the test cell body 102 may be two materials (the same or different) that are joined to achieve fluid coupling. The sampling port 116 includes a sample valve 118 for allowing fluids to flow through the sampling port 116 into and out of the interior 102*a* of the test cell body 102. The sample valve 118 accordingly has an open position and a closed position. When the sample valve 118 is in the open position, bidirectional fluid flow is permitted; when in the closed position, the sample valve 118 prevents flow in both directions. The open and closed position of the sample valve 118 may be achieved by any mechanism that permits or restricts flow therethrough. In one embodiment, the sample valve 118 may have a manual lever 130 for movement in one direction or another (or full clockwise or full counterclockwise movement) to achieve the open and closed positions of the sample valve 118. Other mechanisms may include, but are not limited to electrical, hydraulic, pneumatic actuation, and any combination thereof.

In some embodiments, a flow restriction device may be located anywhere differential pressure can be induced, such as anywhere in the interior 102*a* of the test cell body 102 where the treatment fluid may be located, the open end 114, the sampling port 116, the sample valve 118, and any combination thereof. The term "flow restriction device," and grammatical variants thereof, as used herein, refers to any geometric element which would restrict the flow of a fluid when a force or pressure is applied from the piston 104 or another source. The tapered end 114 and sampling port 116 as illustrated in FIG. 1 would constitute one such example. In some embodiments, the flow restriction device restricts the flow of a fluid (e.g., a treatment fluid) by at least about 10% as it flows through the sampling port and sample valve for collection compared to the flow of the same fluid absent the flow restriction device. Examples of suitable flow restriction devices for use in the embodiments of the present disclosure may include, but are not limited to, a reduced diameter sampling port (e.g., in relation to the test cell body diameter), mesh, screen, orifice, or any combination thereof to restrict flow, which may mimic restricted downhole flow paths or movement through sand screen completion equipment. These devices could also be used to restrict fluid flow through the opening, which would provide a more detailed study of fluid flow behavior.

A sealing assembly 124 is additionally located at the bottommost lower section 102 of the test cell body 102. The sealing assembly 124 is adapted to be inserted into the test cell body 102 where it comes into contact with the interior 102*a* of the test cell body 102 to fluidly seal the open end 114, and accordingly in some embodiments is substantially cylindrical. The sealing assembly provides a fluid seal to ensure that the test cell body 102 can maintain applied pressure (often very high pressures) immediately and over time, as needed. As used herein, the term "fluidly seal," and grammatical variants thereof, refers to a seal formed between at least two elements which prevents significant or any seepage to the external environment of a fluid (i.e., liquid or gas) flowing over the seal. The fluidic seal may be achieved by rubber sealing, metallic sealing, weldment sealing, and the like. The sealing assembly 124 may or may not be removable (i.e., removably connected to the test cell apparatus 100 or non-removable (e.g., welded, metallic or rubber sealed, and the like) and includes a retainable test cell cap 126. One benefit of a removably connected sealing assembly is the added ability to fully clean and inspect the fluid portion of the test cell. The retainable test cell cap 126 may be self-latchable (e.g., forming the entirety of the sealing assembly 124) or may be latchable by a retaining latch. As used herein, the term "latch," and grammatical variants thereof, refers to causing or creating a fluidic seal, and does not imply any particular mechanism.

The retainable test cell cap 126, whether or not it is self-latching, may include rubber sealing components or other sealing mechanisms and generally comes into contact with the open end 114, and may be designed to fit the geometry of the open end 114 (e.g., the tapered open end 114 of FIG. 1). In some embodiments, the retainable test cell cap 126 is self-latchable; in other embodiments, a retaining latch 128 is used to retain the retainable test cell cap 126 in place. The retaining latch 128 may be manually latchable, self-latchable, or a combination thereof such that it is capable of both manual latching and self-latching. The retaining latch 128 may be in the form of a ring, a clamp, a press, or any other latching mechanism, without departing from the scope of the present disclosure. If the retainable test cell cap 126 or the retaining latch 128 is self-latchable, the sealing assembly 124 may be placed in position and then sealing of the retainable test cell cap 126 by the retaining latch 128 is performed without manual intervention, such as by a mechanical mechanism, an electrical mechanism, a spring mechanism, or any other self-latchable mechanism, without departing from the scope of the present disclosure. Even if the retainable test cell cap 126 is self-latchable, it is to be appreciated that the manual latching may also be performed, without departing from the scope of the present disclosure.

All or a portion of the sealing assembly 124 accordingly may surround a portion of the sampling port 116, as shown in FIG. 1. Therefore, the sampling port 116 extends through the sealing assembly 124 and through the sample valve 118 for allowing or preventing fluid flow therethrough.

The uppermost portion of the upper end 108 of the test cell body 102 is a closed end 120, which may be "closable," such that it may be removed, for example to introduce the pressurization fluid 110. The closed end 120 may be characterized as a plug, cap, or otherwise a seal that can be closed to form the closed end 120, such as by one or more screws 120a. It will be appreciated that any configuration capable of maintaining the closed end 120 of the test cell body 102 may be employed, without departing from the scope of the present disclosure. Through the closed end 120 may be a pressure input 122 for pressurizing the interior 102a of the test cell body 102 comprising a treatment fluid 112 (as well as the floating piston 104 and the pressurization fluid 110).

The pressure input 122 may accordingly be fluidly coupled to a pressure control device for supplying pressure to the interior 102a of the test cell body 102 for performing aging testing, including the pressurization fluid 110. The pressurization fluid 110 may be any pressurization fluid capable of handling high temperatures and pressures applied within the interior 102a of the test cell body 102. In some embodiments, the pressurization fluid 110 includes, but is not limited to, hydraulic oil, mineral oil, a hydrocarbon fluid (i.e., selected to withstand the desired applied pressure), an aqueous fluid (e.g., water), a gas, and any combination thereof.

The pressure control device may be any device capable of supplying pressure to the interior 102a. Typically, the test control apparatus 100 of the present disclosure is designed to be operable at pressures in the range of from about 0.1 megapascal (MPa) to about 300 MPa, encompassing any value and subset therebetween. Pressure may be exerted through the pressure input 122 by a pressure control device.

The test cell apparatus 100 is designed not only to test treatment fluids at a wide range of pressures, including elevated pressures, but also a wide range of temperatures, including elevated temperatures. In some embodiments, the test cell apparatus 100 is designed to be operable at a temperature in the range of about 20° C. to about 250° C., encompassing any value and subset therebetween. The test cell apparatus 100 itself may be heated to the desired temperature for the desired period of time or the interior 102a of the test cell body 102 comprising the treatment fluid 112 (and the floating piston 104 and pressurization fluid 110) may be singly heated to the desired temperature for the desired period of time. Heating may be accomplished with any suitable heating devices for applying heat to the test cell apparatus 100 including, but not limited to, cast heaters, ceramic heaters, band heaters, electrical coils, circulating heat exchangers, and any combination thereof.

The test cell apparatus 100 and its components described above may be composed of various materials, provided that they are able to withstand a broad range of temperatures and pressures for use in performing the aging testing described herein when so exposed. Accordingly, for example, the sample valve 118 may experience less temperature and/or pressure than the interior 102a of the test cell body 102.

Typically, the components of the test cell apparatus 100 are composed of a material including, but not limited to, a metal or metal alloy (e.g., steel, aluminum, titanium, and the like), glass, a ceramic, and any combination thereof capable of containing and withstanding the applied pressures and temperatures described herein.

Figure 2:
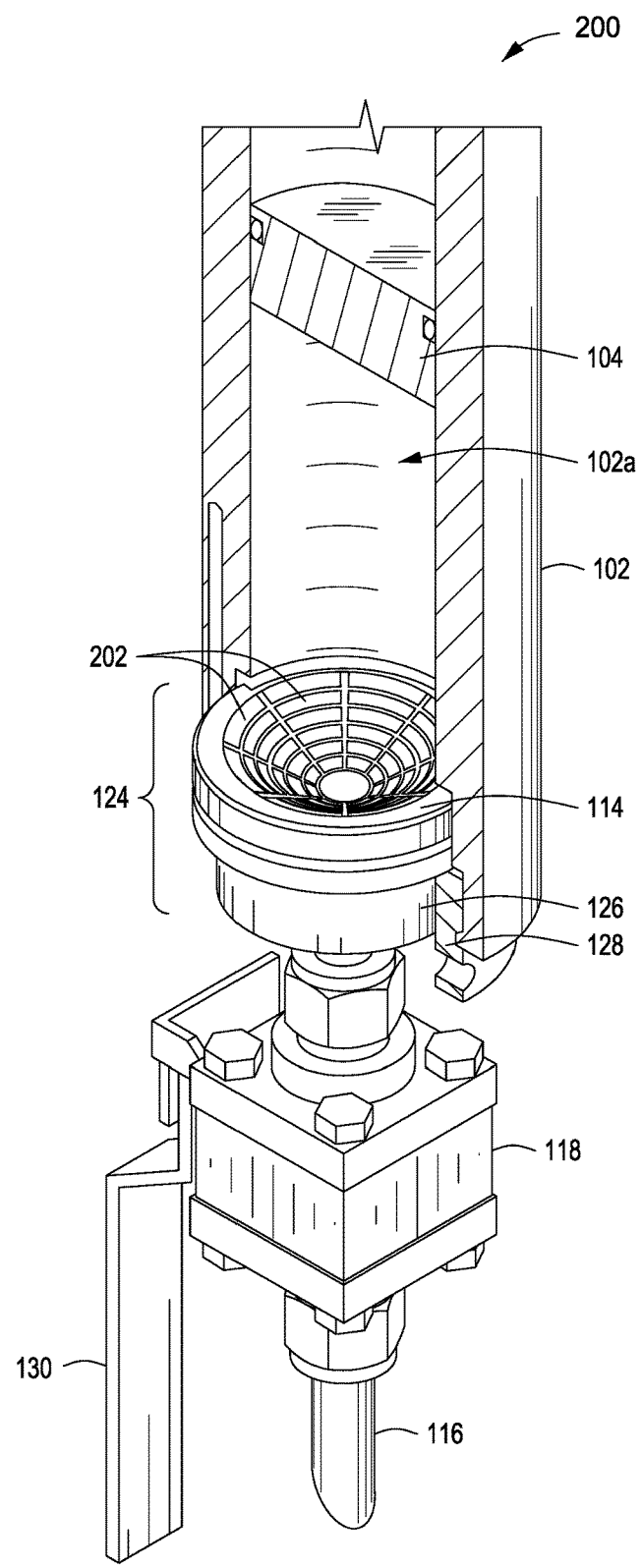
FIG. 2 illustrates a planar view of a test cell apparatus 200 depicting the interior thereof, according to one or more embodiments of the present disclosure.

Referring now to FIG. 2, illustrated is a planar view of a test cell apparatus 200 depicting the interior thereof, according to one or more embodiments of the present disclosure. The testing cell apparatus 200 may be substantially similar or the same as in FIG. 1; accordingly, like numerical labels used in FIG. 1 will be maintained to explain like components in FIG. 2. As shown in FIG. 1 testing apparatus 200 comprises no pressurization fluid or treatment fluid and the interior 102a can be clearly seen as an empty vessel. The floating piston 104 can be seen in the interior 102a of the test cell body 102. The open end 114 is tapered and the sealing assembly 124 is shown having a retainable test cell cap 126 and a retaining latch 128 that is in the form of a retaining ring that circles the outer circumference of the test cell cap 126 on the bottommost portion of the interior 102a of the test cell body 102. A sampling port 116 is shown extending from the open end 114 through the sample valve 118 having a manual lever 130 for movement in one direction or another (or full clockwise or full counterclockwise movement) to achieve the open and closed positions of the sample valve 118. As shown, the sample valve 118 is in the shape of a cube but any shape may be used, provided that the sample valve 118 is able to be placed in an open position and a closed position manually, electrically, and the like.

In some embodiments, as shown, the open end 114 is tapered and further includes conical settling channels 202 in the part of the open end 114 located in the interior 102a of the test cell body 102. The conical settling channels 202 are spaced apart and located along the circumference of the tapered open end 114 portion exposed to the interior 102a. The conical settling channels 202 may be used collect solids located within a treatment fluid to be tested with the test cell apparatus 200. By so collecting, the conical settling channels 202 may reduce or prevent such solids from entering into the sampling port 116, which could partially or wholly plug the path of the sampling port 116 resulting in the inability to perform an accurate aging test.

The treatment fluids described herein may be any treatment fluid for use in performing a subterranean formation operation, as described above, such as a drilling operation. The treatment fluid may be an oil-based treatment fluid, an aqueous-based treatment fluid, an aqueous-miscible treatment fluid, a water-in-oil emulsion treatment fluid, an oil-in-water emulsion treatment fluid, and the like, and any combination thereof. Suitable oil-based treatment fluids may include, but are not limited to, alkanes, olefins, aromatic organic compounds, cyclic alkanes, paraffins, diesel fluids, mineral oils, desulfurized hydrogenated kerosenes, and any combination thereof. Suitable aqueous-based treatment fluids may include, but are not limited to, fresh water, saltwater (e.g., water containing one or more salts dissolved therein), brine (e.g., saturated salt water), seawater, produced water, wastewater, and any combination thereof. Suitable aqueous-miscible treatment fluids may include, but not be limited to, alcohols (e.g., methanol, ethanol, n-propanol, isopropanol, n-butanol, sec-butanol, isobutanol, and t-butanol), glycerins, glycols (e.g., polyglycols, propylene glycol, and ethylene glycol), polyglycol amines, polyols, any derivative thereof, any in combination with salts (e.g., sodium chloride, calcium chloride, calcium bromide, zinc bromide, potassium carbonate, sodium formate, potassium formate, cesium formate, sodium acetate, potassium acetate, calcium acetate, ammonium acetate, ammonium chloride, ammonium bromide, sodium nitrate, potassium nitrate, ammonium nitrate, ammonium sulfate, calcium nitrate, sodium carbonate, and potassium carbonate), any in combination with an aqueous-based fluid, and any combination thereof. Suitable water-in-oil emulsion treatment fluids, also known as invert emulsions, may have an oil-to-water ratio from a lower limit of greater than about 50:50 to an upper limit of less than about 100:0, encompassing any value and subset therebetween. It is to be understood that for water-in-oil and oil-in-water emulsion treatment fluids, any mixture of the above types of base fluids may be used including the water being and/or comprising an aqueous-miscible treatment fluid.

The treatment fluids may further comprise one or more additives that aid in the particular performance of the treatment fluid (e.g., weighting agents added to a drilling fluid). Examples of such additives may include, but are not limited to, a weighting agent, a salt, an inert solid, a fluid loss control agent, an emulsifier, a dispersion aid, a corrosion inhibitor, an emulsion thinner, an emulsion thickener, a viscosifying agent, a gelling agent, a surfactant, a particulate, a proppant, a gravel particulate, a lost circulation material, a foaming agent, a gas, a pH control additive, a breaker, a biocide, a crosslinker, a stabilizer, a chelating agent, a scale inhibitor, a gas hydrate inhibitor, a mutual solvent, an oxidizer, a reducer, a friction reducer, a clay stabilizing agent, and the like, and any combination thereof.

Accordingly, in some embodiments, the present disclosure provides for a means of age testing such treatment fluids and gleaning information regarding sag. Based on such information, the treatment fluid may be manipulated or otherwise re-formulated by altering the type or amount of base treatment fluid, the type or amount of one or more additives, and any combination thereof. That is, the embodiments described herein provide for an aging test method in which a treatment fluid is introduced into the test cell apparatus described above having a pressurization fluid therein. The treatment fluid may be introduced by removing the sealing assembly and introducing the treatment fluid into the test cell body through the sampling port (where the sample valve is in the open position) or directly through the open end of the test cell body if the sampling port is removable from the test cell body. The sealing assembly (and/or the sampling port and sample valve) are replaced and the sample valve is closed to the closed position to prevent the treatment fluid from flowing out of the sampling port, in any order. The test cell apparatus is then turned right side up.

To perform the aging test, at least the inside portion of the test cell body comprising the pressurization fluid and the treatment fluid is exposed to one or both conditions of an elevated pressure and/or an elevated temperature, as described above, such as to mimic the conditions of a particular subterranean formation in which the treatment fluid is to be used. The sample valve is then opened and a portion of the treatment fluid is received as a sample from the sampling port. Thereafter, the sample valve is again closed to the closed position. Multiple stratifications of the treatment fluid can accordingly be tested by receiving multiple samples representing portions of the particular treatment fluid. Before the sample(s) of the treatment fluid are received, at least the inside of the test cell body is allowed to cool and/or de-pressurize (e.g., the pressure is released).

During the aging test, the condition of elevated pressure and/or elevated temperature may be maintained constant or may be altered, such as by adjusting the elevated pressure and/or temperature during the testing or changing the type of condition the treatment fluid is exposed to during the testing. For example, in some embodiments, the elevated pressure and/or temperature may be steadily increased during the testing or steadily decreased during the testing. In another example, the elevated pressure and/or temperature may be stepwise adjusted where large changes are made at intervals over time. During the aging test, the earth's natural gravity is used to apply the same gravitational force to contribute to sag and weight material stratification. The test may also be performed under artificially increased G-force due to a rotational or other force applied to the test assembly. With increased G-force the results of testing may be accelerated to gain insights to the fluid behavior faster than real-time in the natural downhole environment.

In some embodiments, the open end of the test cell body comprises conical settling channels and during testing and sampling of the treatment fluid, solids are collected by the conical settling channels. Accordingly, the solids collected in the conical settling channels form a flow path for the fluid to flow before the solids into the sampling port and sample valve.

The sample(s) taken are measured to determine the density and/or viscosity thereof. Upon determining the density and/or viscosity, the treatment fluid may be deemed appropriate for use in a subterranean formation operation or otherwise manipulated by altering, adding, removing, or adjusting the type or amount of the base fluid, one or more additives, and the like, and any combination thereof to produce an optimized treatment fluid for use in a particular subterranean formation operation. For example, the type or amount of a weighting agent may be added, removed, adjusted (e.g., concentration) for a drilling treatment fluid to optimize the drilling treatment fluid for a particular drilling operation in a particular subterranean formation operation. In other embodiments, the entire treatment fluid may be reformulated and again testing to obtain additional information to optimize the treatment fluid, without departing from the scope of the present disclosure.

Figure 3:
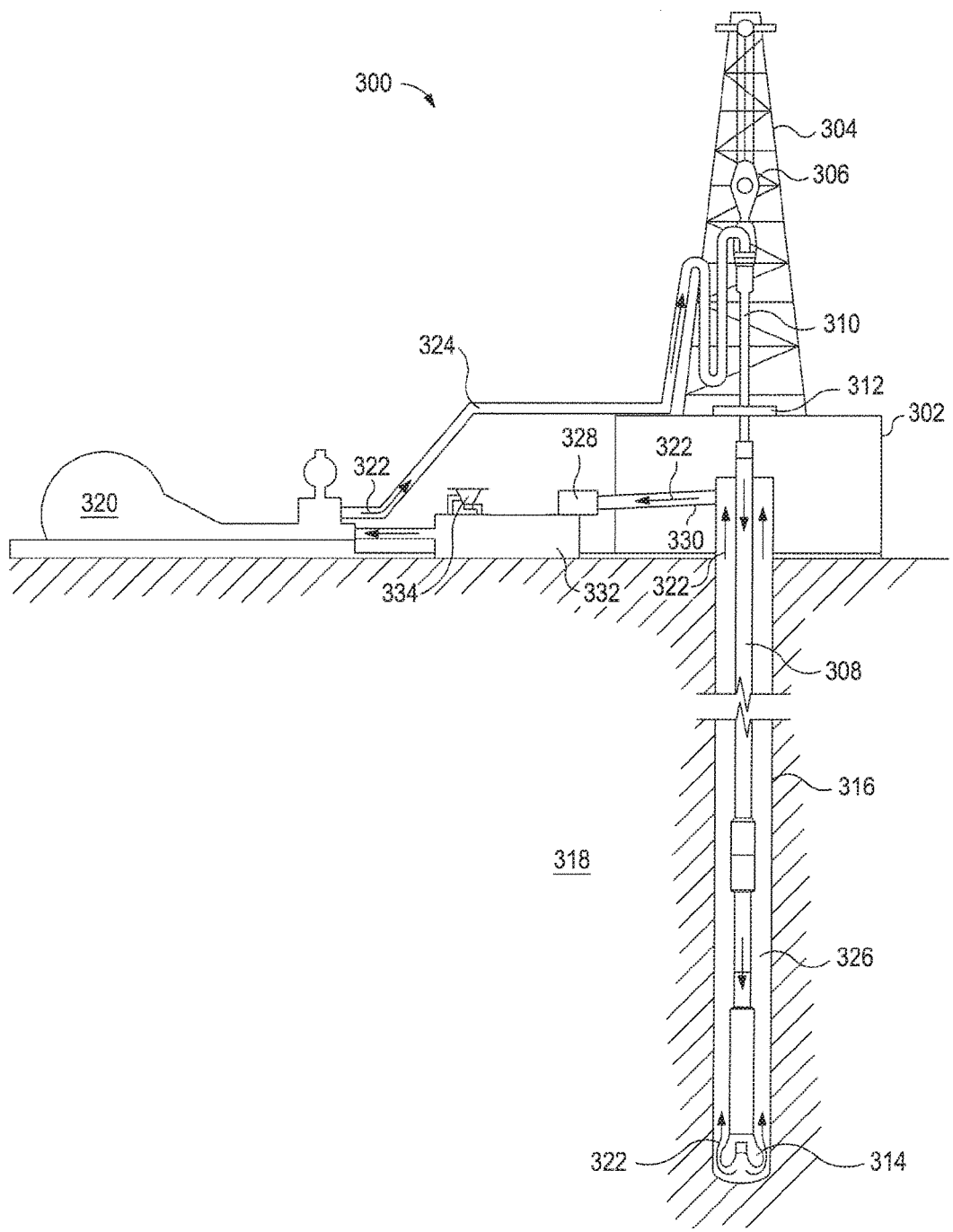
FIG. 3 provides a diagram of a drilling system which may be employed using a drilling treatment fluid after optimization using the test cell apparatus and method of the present disclosure, according to one or more embodiments described herein.

Referring now to FIG. 3, illustrated is a diagram of a drilling system for performing a drilling operation using a treatment fluid optimized using the aging test cell apparatus and method of the present disclosure, according to at least some embodiments described herein. It is to be understood that while FIG. 3 generally depicts a land-based drilling assembly, those skilled in the art will readily recognize that the principles described herein are equally applicable to subsea drilling operations that employ floating or sea-based platforms and rigs, without departing from the scope of the disclosure.

As illustrated, the drilling assembly 300 may include a drilling platform 302 that supports a derrick 304 having a traveling block 306 for raising and lowering a drill string 308. The drill string 308 may include, but is not limited to, drill pipe and coiled tubing, as generally known to those skilled in the art. A kelly 310 supports the drill string 308 as it is lowered through a rotary table 312. A drill bit 314 is attached to the distal end of the drill string 308 and is driven either by a downhole motor and/or via rotation of the drill string 308 from the well surface. As the bit 314 rotates, it creates a wellbore 316 that penetrates subterranean formation 318.

A pump 320 (e.g., a mud pump) circulates drilling treatment fluid 322 (optimized according to the methods described herein) through a feed pipe 324 and to the kelly 310, which conveys the drilling treatment fluid 322 downhole through the interior of the drill string 308 and through one or more orifices in the drill bit 314. The drilling treatment fluid 322 is then circulated back to the surface via an annulus 326 defined between the drill string 308 and the walls of the wellbore 316. At the surface, the recirculated or spent drilling treatment fluid 322 exits the annulus 326 and may be conveyed to one or more fluid processing unit(s) 328 (e.g., shakers) via an interconnecting flow line 330. The one or more fluid processing unit(s) 328 may be useful in removing large drill cuttings, for example. After passing through the fluid processing unit(s) 328, a "cleaned" drilling treatment fluid 322 may be deposited into a nearby retention pit 332 (i.e., a mud pit). While illustrated as being arranged at the outlet of the wellbore 316 via the annulus 326, those skilled in the art will readily appreciate that the fluid processing unit(s) 328 may be arranged at any other location in the drilling assembly 300 to facilitate its proper function, without departing from the scope of the disclosure.

One or more additives (e.g., weighting agents) may be added to the drilling treatment fluid 322 via a mixing hopper 334 communicably coupled to or otherwise fluidly coupled with the retention pit 332. The mixing hopper 334 may include, but is not limited to, mixers and related mixing equipment. In other embodiments, however, additives may be added to the drilling treatment fluid 322 at any other location in the drilling assembly 300. In at least one embodiment, for example, there may be more than one retention pit 332, such as multiple retention pits 332 in series. Moreover, the retention pit 332 may be representative of one or more fluid storage facilities and/or units where additives may be stored, reconditioned, and/or regulated until added to the drilling treatment fluid 322.

While not specifically illustrated herein, the drilling assembly 300 may also include additional components, for example, shakers (e.g., shale shaker), centrifuges, hydrocyclones, separators (e.g., magnetic and electrical separators), desilters, desanders, filters (e.g., diatomaceous earth filters), heat exchangers, fluid reclamation equipment, sensors, gauges, pumps, compressors, conduits, pipelines, trucks, tubulars, pipes, pumps, compressors, motors, valves, floats, drill collars, mud motors, downhole motors, downhole pumps, MWD/LWD tools, tool seals, packers, roller cone bits, PDC bits, natural diamond bits, any hole openers, reamers, coring bits, and the like, and any communication components associated therewith (e.g., wirelines, telemetry components, etc.).

While various embodiments have been shown and described herein, modifications may be made by one skilled in the art without departing from the scope of the present disclosure. The embodiments described here are exemplary only, and are not intended to be limiting. Many variations, combinations, and modifications of the embodiments disclosed herein are possible and are within the scope of the disclosure. Accordingly, the scope of protection is not limited by the description set out above, but is defined by the claims which follow, that scope including all equivalents of the subject matter of the claims.

Embodiments Disclosed herein Include:

Embodiment A: An aging test method comprising: providing a test cell apparatus comprising: a test cell body having an open end for receiving a treatment fluid into an interior of the test cell body, the interior having a floating piston for separating the treatment fluid from a pressurization fluid; a sampling port extending from the open end and having a sample valve for receiving samples of the treatment fluid from the sampling port, the sample valve has an open position and a closed position; a pressure input for pressurizing the interior; and a sealing assembly adapted to be inserted into the test cell body in contact with the interior to fluidly seal the open end and through which the sampling port extends, the sealing assembly comprising a retainable test cell cap; introducing an oilfield treatment fluid into the test cell body; closing the sample valve to the closed position; sealing the open end with the sealing assembly; exposing the oilfield treatment fluid in the test cell body to a condition selected from the group consisting of elevated pressure, elevated temperature, and any combination thereof; opening the sample valve to the open position; receiving at least one sample of the treatment fluid from the sampling port; and closing the sample valve to the closed position.

Embodiment B: An aging test system comprising: a retaining ring; and a test cell apparatus comprising: a test cell body having an open end for receiving a treatment fluid into an interior of the test cell body, the interior having a floating piston for separating the treatment fluid from a pressurization fluid; a sampling port extending from the open end and having a sample valve for receiving samples of the treatment fluid from the sampling port, the sample valve has an open position and a closed position; a pressure input for pressurizing the interior; and a sealing assembly adapted to be inserted into the test cell body in contact with the interior to fluidly seal the open end and through which the sampling port extends, the sealing assembly comprising a retainable test cell cap.

Embodiment C: A test cell apparatus comprising: a test cell body having an open end for receiving a treatment fluid into an interior of the test cell body, the interior having a floating piston for separating the treatment fluid from a pressurization fluid; a sampling port extending from the open end and having a sample valve for receiving samples of the treatment fluid from the sampling port, the sample valve has an open position and a closed position; a pressure input for pressurizing the interior; and a sealing assembly adapted to be inserted into the test cell body in contact with the interior to fluidly seal the open end and through which the sampling port extends, the sealing assembly comprising a retainable test cell cap.

Embodiments A, B, and/or C may have one or more of the following additional elements in any combination:

Element 1: Further comprising receiving at least two samples of the treatment fluid from the sampling port over time.

Element 2: Further comprising determining fluid flow behavior of the treatment fluid.

Element 3: Further comprising determining a measurement selected from the group consisting of a density measurement, a viscosity measurement, and any combination thereof of the at least one sample of the treatment fluid from the sampling port.

Element 4: Further comprising altering the condition or maintaining the condition constant.

Element 5: Wherein the pressure input is fluidly coupled to a pressure control device.

Element 6: Wherein the pressure input is fluidly coupled to a pressure control device and the test cell apparatus is operable at a pressure in the range of 0.1 megapascal (MPa) to about 300 MPa.

Element 7: Wherein the test cell apparatus is operable at a temperature in the range of 20° C. to about 250° C.

Element 8: Wherein the sealing assembly is removably connected to the test cell apparatus.

Element 9: Wherein the open end is tapered and comprises conical settling channels.

Element 10: Wherein the open end is tapered and comprises conical settling channels, and further comprising collecting solids in the treatment fluid with the conical settling channels.

Element 11: Wherein the test cell apparatus further comprises a flow restriction device at a location selected from the group consisting of the interior, the open end, the sampling port, the sample valve, and any combination thereof.

By way of non-limiting example, exemplary combinations applicable to A, B, and C include: 1-11; 1, 2, and 10; 6, 7, 9, and 11; 2 and 5; 3, 8, and 9; 1, 3, 4, and 10; 6 and 8; 3 and 9; 2 and 7; 3, 4, 6, and 8; and any combination of one, more, or all of 1-11, without limitation.

Therefore, the embodiments disclosed herein are well adapted to attain the ends and advantages mentioned as well as those that are inherent therein. The particular embodiments disclosed above are illustrative only, as they may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The embodiments illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

What is claimed is:

1. An method comprising:
   providing a test cell apparatus comprising:
      a test cell body having an open end for receiving a treatment fluid into an interior of the test cell body, the interior having a floating piston for separating the treatment fluid from a pressurization fluid;
      a sampling port extending from the open end and having a sample valve for receiving samples of the treatment fluid from the sampling port, the sample valve has an open position and a closed position;
      a pressure input for pressurizing the interior; and
      a sealing assembly adapted to be inserted into the test cell body in contact with the interior to fluidly seal the open end and through which the sampling port extends, the sealing assembly comprising a retainable test cell cap;
   sealing the open end with the sealing assembly;
   introducing an oilfield treatment fluid into the test cell body, through the sampling port;
   closing the sample valve to the closed position;
   exposing the oilfield treatment fluid in the test cell body to a condition selected from the group consisting of elevated pressure, elevated temperature, and any combination thereof; opening the sample valve to the open position;
   receiving at least one sample of the treatment fluid from the sampling port; and closing the sample valve to the closed position.

2. The method of claim 1, further comprising receiving at least two samples of the treatment fluid from the sampling port over time.

3. The aging test method of claim 1, further comprising determining fluid flow behavior of the treatment fluid.

4. The method of claim 1, further comprising determining a measurement selected from the group consisting of a density measurement, a viscosity measurement, and any combination thereof of the at least one sample of the treatment fluid from the sampling port.

5. The method of claim 1, further comprising altering the condition or maintaining the condition constant.

6. The method of claim 1, wherein the pressure input is fluidly coupled to a pressure control device.

7. The method of claim 1, wherein the pressure input is fluidly coupled to a pressure control device and the test cell apparatus is operable at a pressure in the range of 0.1 megapascal (MPa) to about 300 MPa.

8. The method of claim 1, wherein the test cell apparatus is operable at a temperature in the range of 20° C. to about 250° C.

9. The method of claim 1, wherein the sealing assembly is removably connected to the test cell apparatus.

10. The method of claim 1, wherein the open end is tapered and comprises conical settling channels.

11. The method of claim 1, wherein the open end is tapered and comprises conical settling channels, and further comprising collecting solids in the treatment fluid with the conical settling channels.

12. The method of claim 1, wherein the test cell apparatus further comprises a flow restriction device at a location selected from the group consisting of the interior, the open end, the sampling port, the sample valve, and any combination thereof.

* * * * *